US010517695B2

(12) United States Patent
Van Lierde et al.

(10) Patent No.: US 10,517,695 B2
(45) Date of Patent: Dec. 31, 2019

(54) CUSTOM HEALING CAP FOR DENTAL IMPLANTOLOGY AND METHOD FOR DESIGN AND MANUFACTURING THEREOF

(75) Inventors: Carl Van Lierde, Meerbeke (BE); Tim Van Cleynenbreugel, Kersbeek-Miskom (BE)

(73) Assignee: DENTSPLY SIRONA Inc., York, PA (US)

(*) Notice: Subject to any disclaimer, the term of this patent is extended or adjusted under 35 U.S.C. 154(b) by 287 days.

(21) Appl. No.: 13/704,362

(22) PCT Filed: Jun. 15, 2011

(86) PCT No.: PCT/EP2011/059964
§ 371 (c)(1),
(2), (4) Date: Dec. 14, 2012

(87) PCT Pub. No.: WO2011/157762
PCT Pub. Date: Dec. 22, 2011

(65) Prior Publication Data
US 2013/0089837 A1    Apr. 11, 2013

(30) Foreign Application Priority Data
Jun. 15, 2010   (GB) .................................... 1009999.2

(51) Int. Cl.
*A61C 5/77* (2017.01)
*G16H 20/40* (2018.01)
*A61C 13/00* (2006.01)
*B33Y 80/00* (2015.01)

(52) U.S. Cl.
CPC ............ *A61C 5/77* (2017.02); *A61C 13/0004* (2013.01); *G16H 20/40* (2018.01); *B33Y 80/00* (2014.12)

(58) Field of Classification Search
CPC ...... A61C 13/0004; A61C 5/77; G16H 20/40; B33Y 80/00
USPC .......................................................... 433/223
See application file for complete search history.

(56) References Cited

U.S. PATENT DOCUMENTS

| | | | | | |
|---|---|---|---|---|---|
| 5,273,429 | A | * | 12/1993 | Rekow | A61C 13/0004 433/215 |
| 5,989,029 | A | * | 11/1999 | Osorio | A61C 8/005 433/173 |
| 6,398,554 | B1 | * | 6/2002 | Perot | A61C 13/0004 433/218 |
| 6,835,066 | B2 | * | 12/2004 | Iiyama | A61C 13/0004 433/215 |

(Continued)

FOREIGN PATENT DOCUMENTS

| WO | 2007/062658 A2 | 6/2007 |
|---|---|---|
| WO | 2009/094576 A1 | 11/2009 |

*Primary Examiner* — Cris L. Rodriguez
*Assistant Examiner* — Hao D Mai
(74) *Attorney, Agent, or Firm* — Dentsply Sirona Inc.

(57) ABSTRACT

A computer based method is used to design a healing cap of an implant. The method is based on a 3D computer plan of the implant that includes digital representations of positions of implants in the mouth of the patient. The method comprises loading 3D implant plan into a computer and combining the 3D implant plan with information about a prosthetic setup. The method determines a marginal edge of a healing cap of an implant based on a 3D representation of the existing patient anatomy, the 3D implant plan and the prosthetic set-up. The healing cap is then manufactured to the custom design.

23 Claims, 4 Drawing Sheets

(56) References Cited

U.S. PATENT DOCUMENTS

| | | | | |
|---|---|---|---|---|
| 7,004,754 B2* | 2/2006 | Kaufmann | ............... | A61C 7/00 433/213 |
| 7,661,956 B2* | 2/2010 | Powell | ............... | A61C 13/0004 433/172 |
| 7,762,814 B2* | 7/2010 | van der Zel | ........... | A61C 1/084 433/201.1 |
| 7,899,221 B2* | 3/2011 | Weber | ................ | A61C 13/0004 382/128 |
| 7,901,209 B2* | 3/2011 | Saliger | ................ | A61C 8/0048 433/215 |
| 2005/0186540 A1* | 8/2005 | Taub | ........................ | A61C 5/10 433/223 |
| 2006/0040236 A1* | 2/2006 | Schmitt | ........................ | 433/213 |
| 2006/0063135 A1* | 3/2006 | Mehl | ................. | A61C 13/0004 433/223 |
| 2006/0183082 A1* | 8/2006 | Quadling | ........... | A61C 13/0004 433/223 |
| 2007/0154868 A1* | 7/2007 | Scharlack | ................ | A61C 5/10 433/215 |
| 2009/0111071 A1* | 4/2009 | Yau | .................... | A61C 13/0004 433/173 |
| 2009/0248184 A1* | 10/2009 | Steingart et al. | ............... | 700/98 |
| 2010/0105011 A1* | 4/2010 | Karkar | .................. | A61C 1/084 433/215 |
| 2010/0151417 A1* | 6/2010 | Nilsson | ............... | G06F 19/3437 433/167 |
| 2011/0171604 A1* | 7/2011 | Durbin | .................... | A61C 5/08 433/213 |
| 2012/0064489 A1* | 3/2012 | Rubbert | ................ | A61C 5/007 433/175 |
| 2012/0123576 A1* | 5/2012 | Pettersson | ........... | G06F 19/3437 700/98 |

* cited by examiner

CUSTOM HEALING CAP FOR DENTAL IMPLANTOLOGY AND METHOD FOR DESIGN AND MANUFACTURING THEREOF

FIELD OF THE INVENTION

The present invention relates to Dental Implantology and in particular to a custom healing cap for dental implantology and a method for use, design and manufacture thereof.

DESCRIPTION OF THE RELATED ART

Implant dentistry involves the restoration of one or more teeth in a patient's mouth using artificial components. The process of restoring a tooth can be carried out in two stages.

Figure 1:
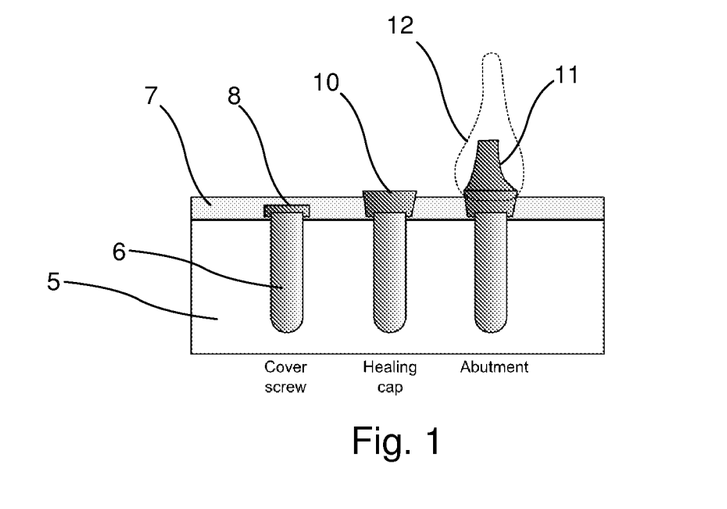
FIG. 1 shows components used in implant dentistry.

Stage 1 involves implanting the dental implant 6 into the bone of a patient's jaw 5. After the implant 6 is initially installed in the jawbone 5, a cover screw 8 is placed over the exposed proximal end in order to seal the internal screw hole or connection cavity and prevent soft tissue growth into the internal thread of the implant. The patient's soft tissues 7 are then sutured over the implant to allow the implant site to heal and allow desired osseointegration to occur. Complete osseointegration typically takes anywhere from four to ten months. Alternatively, immediately after implant placement a temporary healing cap 10 can be placed instead of the cover screw that protrudes through the gingiva to support the soft tissue during implant osseointegration. Instead of a healing cap 10, a standard abutment 11 can be placed on which a provisional restoration is fixed (immediate loading).

During stage 2, the cover screw 8 or healing cap 10 is removed, exposing the proximal end of the implant 6. An appropriately sized final abutment is screwed on the implant 6 and the final restoration 12 is installed on the abutment. In case of a cover screw, an incision is required through the patient's mucosal tissue to expose the implant. In case of a healing cap 10, this can be replaced by the final abutment without the need for an incision. In case of immediate loading the abutment can be reused or replaced by a final abutment. In many cases the final abutment has a customized design for optimal prosthetic and aesthetic outcome.

When a cover screw is used during the osseointegration of the implant, the screw is completely covered by the gingiva. As a result it cannot be used to shape the soft tissue during implant healing. Moreover, access of the implant for installation of the final abutment requires a second incision, thereby damaging the soft tissue that will surround the abutment.

The use of a healing cap has two functions. Firstly, it closes the internal (threaded) opening of the implant, thereby preventing soft tissue growth into the implant internal thread. The healing cap should cover the perimeter of the implant shoulder. This prevents regrowth of gingival tissue around the shoulder of the implant. Secondly, it allows the soft tissue to heal around the area of the incision, leave an opening or sulcus for the abutment and prosthetic tooth.

When a standard healing cap is used, in many cases the shape and longitudinal axis of the cap differ from those of the final abutment. As a consequence, the healing cap leaves a gap around the base of the prosthetic tooth, which may capture food particles and can lead to infection and possible gum disease. Moreover, the gap is visible and is aesthetically unpleasant, particularly for front teeth.

While custom abutments are known with a design specific for a certain implant site and thus soft tissue profile, they do not allow for a removable prosthesis to be used during the healing period i.e. osseointegration period of the implants. Moreover, since they are designed after the implants have been installed in the mouth of the patient, they do not lend themselves for immediate loading and shaping the soft tissue.

SUMMARY OF THE INVENTION

The invention presented here concerns a custom healing cap and a method and system for design and manufacturing thereof prior to dental implant placement.

An aspect of the present invention provides a method for providing a custom healing cap of a dental implant, the method being based on a 3D computer plan of the implant comprising digital representations of positions of the implant in the mouth of the patient. The method comprises loading the 3D implant plan into a computer, combining the 3D implant plan with information about a prosthetic setup, determining a marginal edge of the healing cap of the implant based on a 3D representation of an existing patient anatomy, the 3D implant plan and the prosthetic set-up, wherein the healing cap is adopted to support the soft tissue and to shape it according to the desired emergence profile for prosthetic restoration, and storing the determined marginal edge in memory. The desired emergence profile, which is the desired outcome, is defined in function of simulated soft tissue profile. The design of the custom healing cap is based on one or more of the following:

- A computer plan of the desired 3D implant comprising digital representations of positions in the mouth of the patient. The 3D computer plan can be created based on grey value data of the patient, acquired from CT, CBCT, MRI or the like. The grey value data contains information about the level (i.e. thickness, profile, etc.) of the soft tissue (gums) along the jaw of the patient.
- The desired prosthetic setup, including the desired emergence profile of the crown.
- The soft tissue situation prior to implant placement including soft tissue geometry in digital data. The desired gingiva shape and contour, which depends on the bone level and biotype of the patient (i.e. type and thickness of the soft tissue).

The emergence profile of the crown of a tooth from the gingiva should have a natural appearance in order to achieve an aesthetically pleasing result. The emergence profile is largely determined by the shape of the soft tissue surrounding the crown. The custom healing cap provides shaping of the soft tissue to the desired contour in the healing phase of the implant, before the final restoration is installed.

A benefit of an embodiment of the invention is that the custom healing cap can be designed before the installation of the implants in the mouth of the patient.

A benefit of an embodiment of the invention is that the custom healing cap can be placed immediately subsequent to implant installation.

A benefit of an embodiment of the invention is that the custom healing cap supports the soft tissue and shapes it according to the desired emergence profile for the prosthetic restoration (i.e. the tooth).

The marginal edge can be defined as a 3D curve defining the transition between the lower, sub-gingival part of the cap, and its upper half. This can be also be described as the 3D curve (closed curve) at the gum level. The healing cap is entirely custom with exception of the connection to the implant. The design is dictated by factors such as the shape of the marginal edge (i.e. the 3D curve), the thickness of the soft tissue at the implant site and the surface curvature of the gums at the implant site. The surface curvature of the gums at the implant site can be used to define the shape of the dome.

Advantageously, the method further comprises manufacture of the healing cap. Manufacture can be performed by techniques such as CNC milling, Rapid Prototyping, Rapid Manufacturing or layered manufacturing.

The present invention also provides a computer based design system that when executed on a processing engine executes and of the methods for providing a custom healing cap including manufacturing the healing cap by CNC milling or rapid prototyping or rapid manufacturing or layered manufacturing or a computer system for providing a custom healing cap.

The present invention also provides a computer program product for manufacture of the healing cap. The healing cap may be manufactured by CNC milling, rapid prototyping, rapid manufacturing or layered manufacturing. The computer program product for carrying out the method of the present invention can reside in any suitable memory and the present invention applies equally regardless of the particular type of signal bearing media used to actually store the computer program product. Examples of computer readable signal bearing media include: recordable type media such as floppy disks and CD ROMs, solid state memories, tape storage devices, magnetic disks.

BRIEF DESCRIPTION OF THE DRAWINGS

Embodiments of the invention will be described, by way of example only, with reference to the accompanying drawings in which.

DETAILED DESCRIPTION

The present invention will be described with respect to particular embodiments and with reference to certain drawings but the invention is not limited thereto but only by the claims.

A custom healing cap enables soft tissue management to achieve an optimal aesthetic outcome of the implant treatment once the final restoration is placed. By taking into account the desired emergence profile of the crown and the soft tissue situation prior to implant placement, a healing cap can be designed in such a way that it exerts the right pressure on the soft tissue to achieve the desired soft tissue shape for the final restoration. The nature of the surgical technique during implant installation (e.g. punching the gum tissue or making an incision) does not influence the final soft tissue shape.

Suitable indications for the use of a custom healing cap include but are not limited to aesthetically demanding cases where:

The jaw is partially edentulous and an implant is placed next to a natural tooth. Soft tissue management of the papilla of the natural tooth and the soft tissue at the implant site is required to achieve an aesthetically pleasing result and a natural appearance.

A natural tooth is extracted and immediately replaced by an implant. Soft tissue management is required to preserve the natural appearance of the soft tissue surrounding the extracted tooth.

Figure 2:
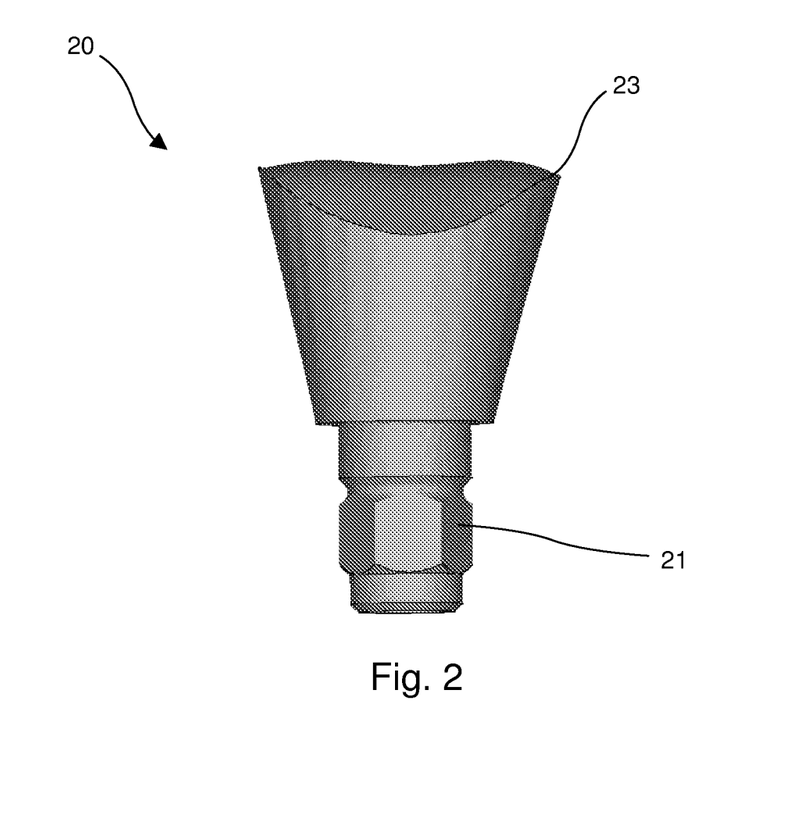
FIG. 2 shows a healing cap.
Figure 3:
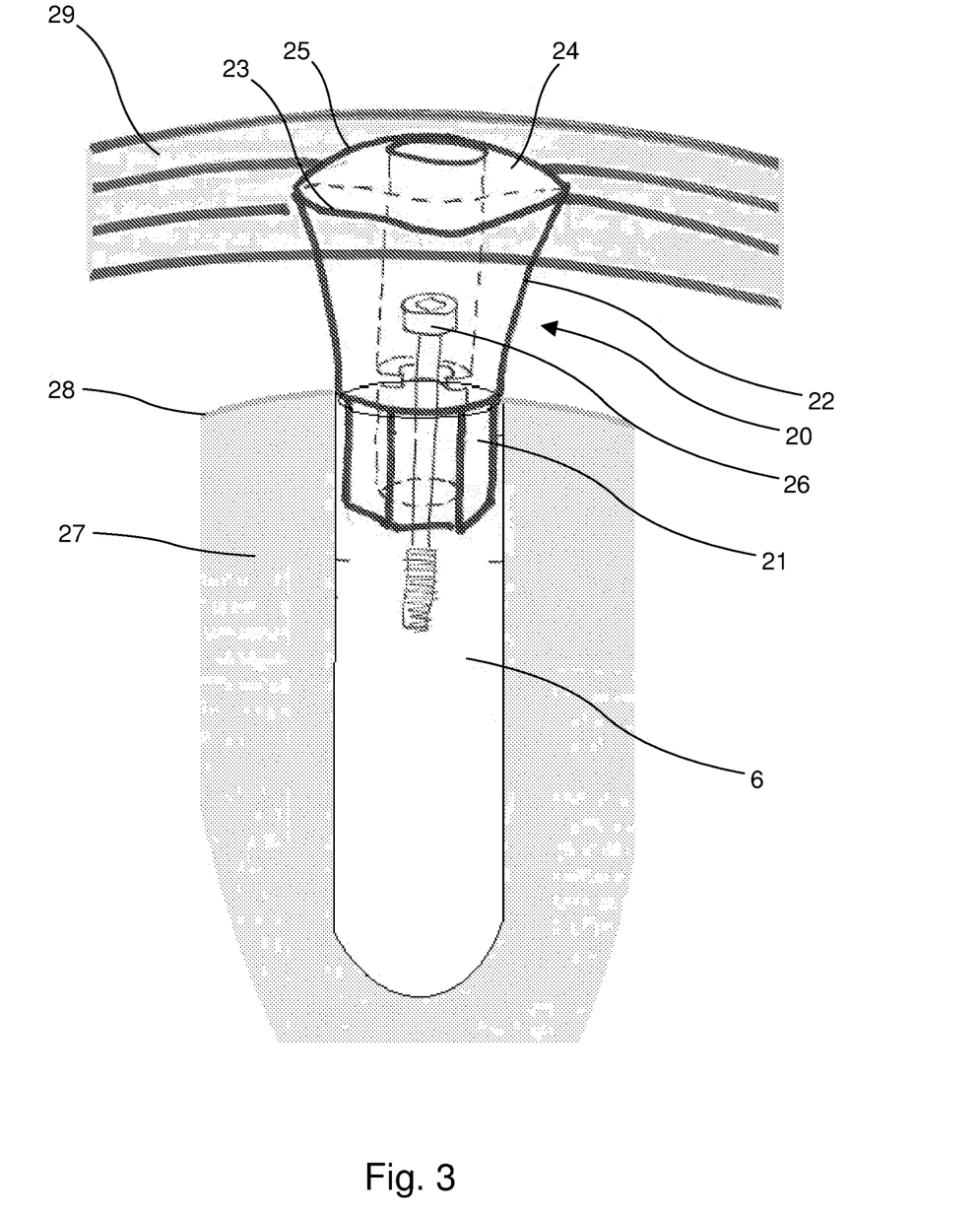
FIG. 3 shows a healing in position in a patient's mouth.

FIGS. 2 and 3 show a custom healing cap. FIG. 2 shows the healing cap 20 by itself. FIG. 3 shows the healing cap in position in a patient's mouth. An implant 6 is mounted in a patient's jaw bone 27. The implant extends to the bone level 28. A healing cap 20 according to an embodiment of the invention is fitted to the upper end of the implant 6. The lower end of the healing cap has an interface or connection 21 for interfacing with the upper end of the implant 6. Typically, the interface 21 design is specific to an implant line and brand and is not custom. A fixing (e.g. screw 26) secures the healing cap 20 to the implant 6. The healing cap 20 has a marginal edge 23. This is a 3D curve defining the transition between the lower, sub-gingival part 22 of the cap, and its upper part 24. This can be also be described as the 3D curve (closed curve) at the gum level 29. The lower part 22 of the healing cap 20 sits below the soft tissue surface 29 i.e. caudally with respect to the marginal edge 23. The upper part 24 extends cranially with respect to the marginal edge 23. The upper-most surface 25 of the healing cap 20 can be dome shaped, for example.

Figure 4:
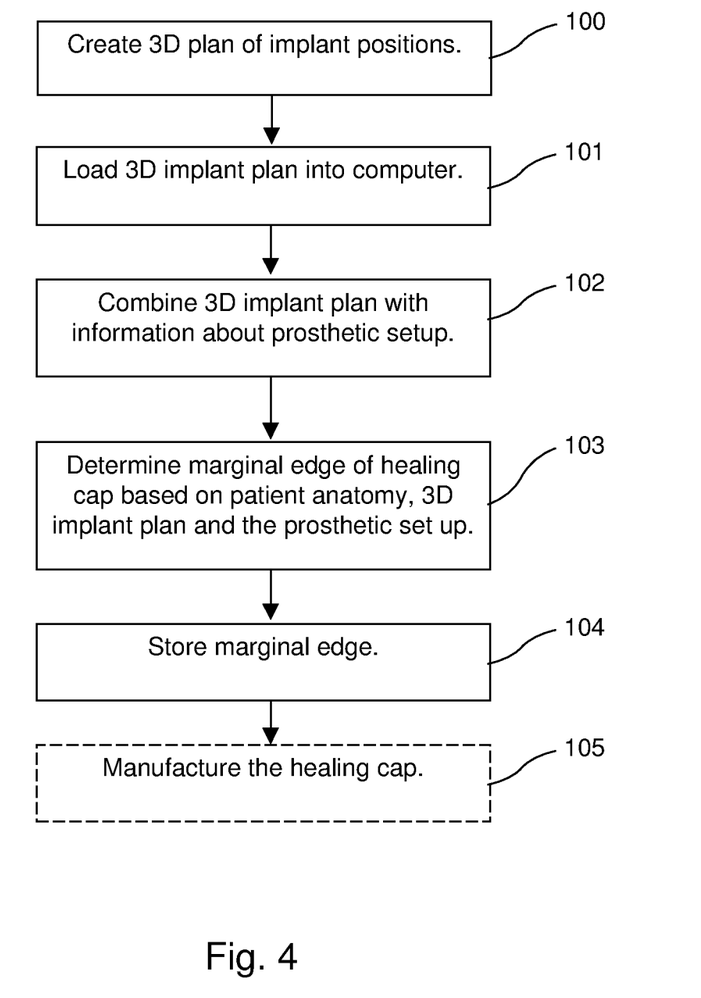
FIG. 4 shows a method to design a healing cap.
Figure 5:
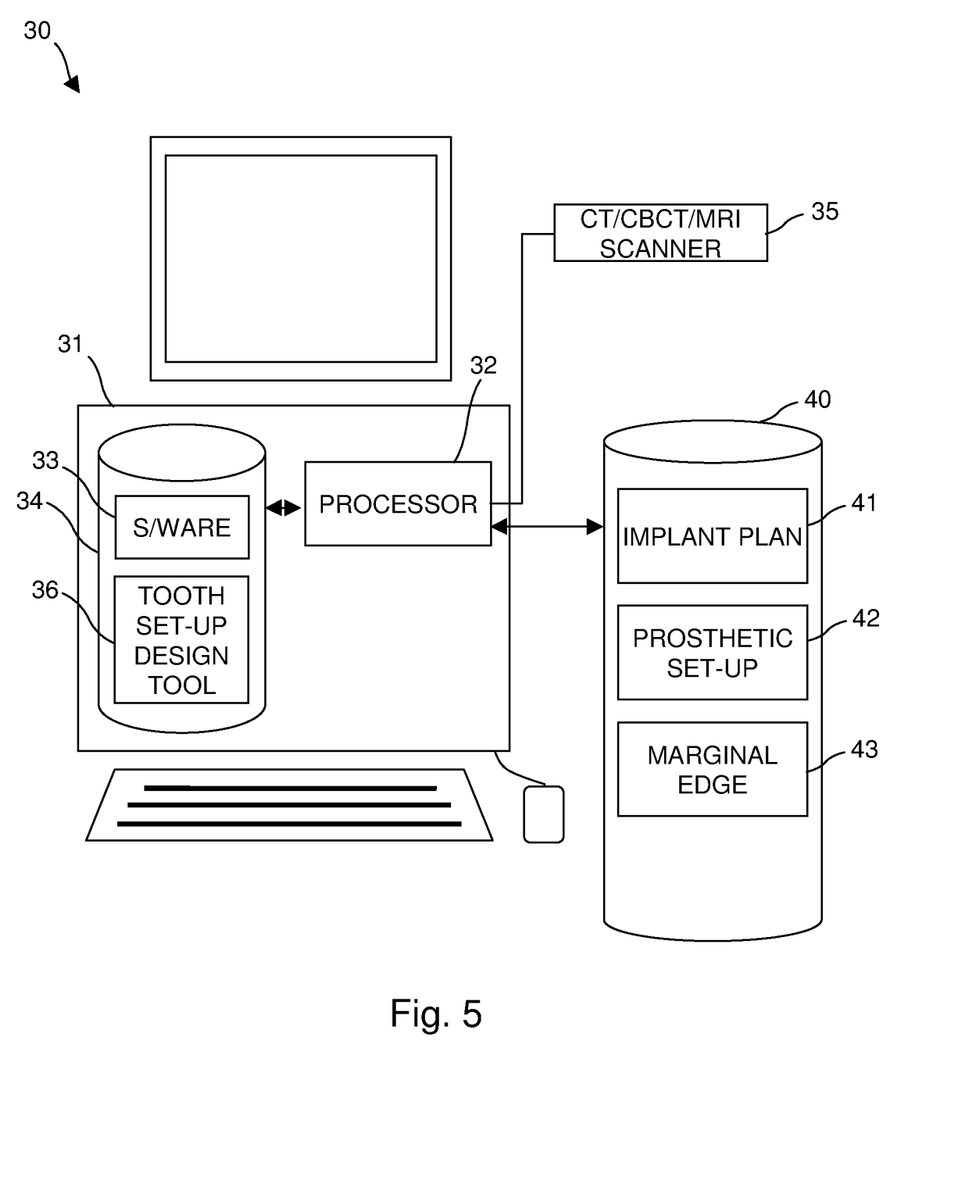
FIG. 5 shows a system used to design a healing cap.

FIG. 4 shows a method according to an embodiment of the invention and FIG. 5 shows a system 30 for implementing the method. The system 30 comprises a computer 31. The computer 31 may be used in a computer based method for a healing cap of an implant, the method being based on a 3D computer plan of the implant comprising digital representations of positions of implants in the mouth of the patient, the method comprising:

loading the 3D implant plan into a computer;
combining the 3D implant plan with information about a prosthetic setup;
determining a marginal edge of a healing cap of an implant based on a 3D representation of the existing patient anatomy, the 3D implant plan and the prosthetic set-up; and
storing the determined marginal edge in memory.

The computer can comprise a processor 32 and memory 34 which stores machine-readable instructions (software) 33 which, when executed by the processor 32, cause the processor to perform the described method. FIG. 5 is a schematic representation of a computing system which can be utilized with the methods and in a system according to the present invention including computer programs such as 3-Matic™ as supplied by Materialise N.V., Leuven, Belgium. The computer may include a video display terminal, a data input means such as a keyboard, and a graphic user interface indicating means such as a mouse. The Computer may be implemented as a general purpose computer, e.g. a UNIX workstation or a personal computer.

The Computer includes a Central Processing Unit ("CPU"), such as a conventional microprocessor of which a Pentium processor supplied by Intel Corp. USA is only an example, and a number of other units interconnected via bus system. The bus system may be any suitable bus system. The computer includes at least one memory. Memory may include any of a variety of data storage devices known to the skilled person such as random-access memory ("RAM"), read-only memory ("ROM"), and non-volatile read/write memory such as a hard disc as known to the skilled person. For example, the computer may further include random-access memory ("RAM"), read-only memory ("ROM"), as well as a display adapter for connecting the system bus to a video display terminal, and an optional input/output (I/O) adapter for connecting peripheral devices (e.g., disk and tape drives) to the system bus. The video display terminal can be the visual output of computer, and can be any suitable display device such as a CRT-based video display well-known in the art of computer hardware. However, with a desk-top computer, a portable or a notebook-based computer, the video display terminal can be replaced with a LCD-based or a gas plasma-based flat panel display. The computer further includes a user interface adapter for connecting a keyboard, mouse, and optional speaker.

The computer also includes a graphical user interface that resides within machine-readable media to direct the operation of the computer. Any suitable machine-readable media may retain the graphical user interface, such as a random access memory (RAM), a read-only memory (ROM), a magnetic diskette, magnetic tape, or optical disk (the last three being located in disk and tape drives). Any suitable operating system and associated graphical user interface (e.g., Microsoft Windows, Linux) may direct CPU. In addition, computer includes a control program that resides within computer memory storage. Control program contains instructions that when executed on CPU allow the computer to carry out the operations described with respect to any of the methods of the present invention.

Those skilled in the art will appreciate that the hardware represented in FIG. 5 may vary for specific applications. For example, other peripheral devices such as optical disk media, audio adapters, or chip programming devices, such as PAL or EPROM programming devices well-known in the art of computer hardware, and the like may be utilized in addition to or in place of the hardware already described.

The computer program product for carrying out the method of the present invention can reside in any suitable memory and the present invention applies equally regardless of the particular type of signal bearing media used to actually stre the computer program product. Examples of computer readable signal bearing media include: recordable type media such as floppy disks and CD ROMs, solid state memories, tape storage devices, magnetic disks.

Accordingly, the present invention also includes a software product which when executed on a suitable computing device carries out any of the methods of the present invention. Suitable software can be obtained by programming in a suitable high level language such as C and compiling on a suitable compiler for the target computer processor. Such methods will now be described.

According to the step 100 of the method, a 3D computer plan 41 of the desired implant positions is created based on grey value data (CT, CBCT, MRI or the like) of the patient. This can be acquired using a scanner 35 controlled by the system 30, or data can be acquired by a separate scanner. The grey value data may also contain information about the level (i.e. thickness, profile, etc.) of the soft tissue (gums) along the jaw of the patient. This information however can also be obtained via different means such an intraoral scan (optical), a scan of the dental impression or plaster model of the jaw, probing or the like. According to an alternative, the 3D implant plan is created as described in patent application US2009/0187393.

At step 101 the 3D implant plan 41 is loaded into a computer.

At step 102 the 3D implant plan 41 is combined with information 42 about the desired prosthetic setup. This information 42 is available either by digitizing a traditional diagnostic wax-up (tooth setup) manufactured by the dental lab either directly (via an optical scan) or indirectly (via use of a scan prosthesis and a second grey value scan). Alternatively, the desired tooth setup is created digitally e.g. digitally mimicking the traditional process of a creating the setup in the dental lab. This step may include the use of software tools 36 such as a virtual articulator.

Based on the known condition of the patient i.e. 3D representation of the existing patient anatomy, the 3D implant plan 41 and the desired prosthetic end-result 42, the design of the custom healing cap is made at step 103. During this step, the desired marginal edge (i.e. the 3d curve defining the transition between the lower, sub-gingival part of the cap and its upper half) of the healing cap is designed. Typically this edge is designed no lower than 1 mm above the existing local soft tissue level. The marginal edge and sub-gingival part are designed such as to force the existing soft tissue to take on the shape of a papilla. Hereto the geometry of the cap is tuned as to either apply or relieve pressure in certain zones of the existing soft tissue around the identified implantation site. During this stage the connection of the healing cap to the implant is also defined, in function of the implant brand and line planned to be used in the mouth of the patient. The connection can be obtained from a digital library. The marginal edge 43 is stored in memory 40 at step 104.

According to another embodiment the marginal edge of the healing abutment is designed according to the expected shape of the soft tissue after healing. Hereto models can be used to predict soft tissue growth/regeneration. These models can include biomechanical, mathematical models as well as empirically determined models e.g. based on statistical analyses of real cases.

The design of the upper half of the cap can be shaped liked a dome and has no protrusions in order to allow the use of a removable (i.e. loose) prosthesis during osseointegration of the implants. Other shapes are possible. The principle idea is that is upper part has a smooth surface with no protusions via which the implant would be loaded or which may hinder the patient during the healing of the implant.

At step 105 the obtained custom healing cap design is subsequently processed (e.g. calculating milling paths or 3D slicing) and sent to a computer driven manufacturing equipment e.g. CNC milling equipment or Rapid Prototyping/Rapid Manufacturing machines for production. Hence methods of the present invention include transmitting the custom healing cap design to a near or remote location, e.g. a CAD/CAM processing facility to manufacture the cap (as described above) in accordance with the details provided by computer.

Such a CAD/CAM manufacturing unit may be connected via a communications to a data network such as the Internet, an Intranet a Local or Wide Area network (LAN or WAN) or a CAN. The manufacturing unit may receive a descriptor file suitable for the manufacture of the cap (as described above), either directly or alternatively indirectly on a suitable signal storage medium such as a diskette, a replaceable hard disc, an optical storage device such as a CD-ROM or DVDROM, a magnetic tape or similar.

The same method as described above could be used when designing a custom abutment rather than a custom healing cap prior to implant placement, and installing the custom abutment at the time of surgery ('immediate loading'). This however has a number of drawbacks:

Not all dental implant cases are suitable for immediate loading. Bone quality, primary implant stability and clinical conditions may require a non-loaded healing time of the implant.

Custom abutments require the use of a pre-fabricated provisional fixed restoration, which includes an additional cost. A healing cap allows the use of a removable prosthesis during implant healing.

Further, the present invention provides a computer program product which includes code segments which when executed on a computer processing engine provides a design method for a healing cap of an implant, the computer program product being adapted to make use of a 3D computer plan of the implant comprising digital representations of positions of implants in the mouth of the patient. The software is adapted to allow loading the 3D implant plan into a computer; combining the 3D implant plan with information about a prosthetic setup; determining a marginal edge of a healing cap of an implant based on a 3D representation of the existing patient anatomy, the 3D implant plan and the prosthetic set-up; and storing the determined marginal edge in memory.

The software when executed on a processing engine is adapted to make use of the prosthetic set-up being a digitized diagnostic wax-up or tooth set-up. The software when executed on a processing engine is adapted to use a tooth set-up created digitally. The software when executed on a processing engine is adapted use of software tools such as a virtual articulator. The software when executed on a processing engine is adapted to make use of a 3D computer plan is created based on grey value data of the patient. The grey value data may contain information about the level of the soft tissue along the jaw of the patient. The software when executed on a processing engine is adapted to make use of information obtained by one or more means such as an intraoral scan (optical), a scan of the dental impression or plaster model of the jaw, probing. The software when executed on a processing engine is adapted to make use of a desired prosthetic setup including the desired emergence profile of the crown.

The software when executed on a processing engine is adapted to make use of a gingiva shape and contour. The software when executed on a processing engine is adapted to make use of an edge designed no lower than 1 mm above the existing local soft tissue level as seen in the representation of the patient anatomy. The software when executed on a processing engine is adapted to make use of mathematical models to simulate soft tissue (i.e. gums and gingival) regeneration.

The software when executed on a processing engine is adapted to allow storing of the connection of the healing cap to the implant. The software when executed on a processing engine is adapted to obtain the connection from a digital library.

The software when executed on a processing engine is adapted to allow manufacture of the healing cap, optionally by CNC milling or Rapid Prototyping or Rapid Manufacturing or layered manufacturing. For this purpose the software when executed on a processing engine is adapted to generate descriptions of layers of the healing cap, each layer being suitable for sequential and contiguous formation by CNC milling or Rapid Prototyping or Rapid Manufacturing or layered manufacturing.

Modifications and other embodiments of the disclosed invention will come to mind to one skilled in the art having the benefit of the teachings presented in the foregoing descriptions and the associated drawings. Therefore, it is to be understood that the invention is not to be limited to the specific embodiments disclosed and that modifications and other embodiments are intended to be included within the scope of this disclosure. Although specific terms may be employed herein, they are used in a generic and descriptive sense only and not for purposes of limitation.

The invention claimed is:

1. A computer based design method for designing a temporary custom healing cap used with a standard implant at an implantation site, comprising:

scanning the implantation site or an impression of the implantation site;

creating a 3-D computer plan of the implant comprising digital representations of possible positions of the implant in the mouth of the patient based on a first grey value data scan of the patient, the first grey value data scan providing first grey value data including information about a thickness and/or a profile of the soft tissue of the patient along a jaw line prior to implant placement;

loading the 3-D implant plan into a computer;

providing information about a desired prosthetic set-up including a desired emergence profile of a prosthetic restoration;

loading the information about a desired prosthetic set-up into the computer;

providing a 3-D representation of the patient anatomy;

loading the 3-D representation of the patient anatomy into the computer;

combining the 3-D implant plan with information about the desired prosthetic setup and the 3-D representation of the patient anatomy, the desired prosthetic setup including a desired emergence profile;

determining growth of said soft tissue after healing using one or more models selected from the group comprising biomechanical, mathematical and empirical models, designing a desired marginal edge using the determined soft tissue growth by defining a closed 3-D curve at gum level that defines a transition between a lower, sub-gingival part of the healing cap and a coronal part of the healing cap;

designing the healing cap using the desired marginal edge, a thickness of the soft tissue and a surface curvature of the gum at said implantation site by defining said coronal part of the healing cap to extend cranially with respect to the desired marginal edge so as to attain a dome-like shape having no protrusions or substantially no protrusions in order to allow the use of a removable prosthesis during healing, wherein the surface curvature of the gum at said implantation site is used to define the dome-like shape;

wherein in said step of designing the healing cap, the healing cap is configured to support soft tissue and to shape the soft tissue according to the desired emergence profile for a prosthetic restoration around said implantation site and storing the desired marginal edge in a memory of the computer.

2. The method of claim 1 wherein the step of creating a 3-D computer plan of the implant comprising digital representations of possible positions of the implant in the mouth of the patient based on a first grey value data scan of the patient further comprises using a scanner for obtaining the first grey value data.

3. The method of claim 1 wherein the step of creating a 3-D computer plan of the implant comprising digital representations of possible positions of the implant in the mouth of the patient based on a first grey value data scan of the patient further comprises using an optical intraoral scan of the patient.

4. The method of claim 1 wherein the step of creating a 3-D computer plan of the implant comprising digital representations of possible positions of the implant in the mouth of the patient based on a first grey value data scan of the patient further comprises using a scan of a dental impression or plaster model of the jaw of the patient.

5. The method of claim 1, wherein the step of providing information based on the prosthetic set-up is obtained from digitized diagnostic wax-up or tooth set-up manufactured by a dental lab either directly by an optical scan or indirectly by use of a scan prosthesis and a second grey value scan.

6. The method of claim 1 wherein the step of providing information based on the prosthetic set-up is obtained using software tools.

7. The method of claim 6 wherein software tools used for the prosthetic set-up includes a virtual articulator.

8. The method of claim 6 wherein the software tools provide a desired emergence profile of a crown.

9. The method of claim 6 wherein the software tools further utilize gingiva shape and contour.

10. The method of claim 1 wherein the step of providing information based on the desired prosthetic set-up is obtained by digitally creating the desired tooth setup.

11. The method of claim 1 further including an additional step of processing the designed healing cap and sending it to one of computer driven manufacturing equipment or rapid prototyping/rapid manufacturing machines.

12. The method of claim 11 wherein the step of processing and sending the designed healing cap to one of computer driven manufacturing equipment or rapid prototyping/rapid manufacturing machines further includes generating descriptions of layers of the healing cap, each layer being suitable for sequential and contiguous formation by the manufacturing machines.

13. The method of claim 1 further comprising designing the coronal part of the healing cap to have the shape of a dome and no protrusions in order to allow the use of removable prosthesis during osseointegration.

14. The method of claim 1 wherein the 3-D computer plan is created based on the grey value data of the patient's gums.

15. The method of claim 1 wherein the desired marginal edge is designed to be no lower than 1 mm above existing local soft tissue, the desired marginal edge and the sub-gingival part of the healing cap are configured for forcing existing soft tissue to take the shape of a papilla.

16. The method of claim 1 further including a step of storing a connection of the temporary healing cap to the implant.

17. A computer based design method for a removable temporary custom healing cap used with an implant at an implantation site, the method being based on a 3D computer plan of the implant using digital representations of positions of the implant in a mouth of a patient, the method comprising the steps of:
scanning the implantation site or an impression of the implantation site;
creating a 3-D implant plan of the implant comprising digital representations of possible positions of the implant based on grey value data of the patient, the grey value data including information about a thickness and/or a profile of the soft tissue of the patient along a jaw line prior to dental implant placement, the plan including an emergence profile for shaping of soft tissue by the healing cap subsequent to installing the implant;
loading the 3-D implant plan into a computer;
providing information about a desired prosthetic set-up;
loading the information about a desired prosthetic set-up into the computer;
providing a 3-D representation of the patient anatomy;
loading the 3-D representation of the patient anatomy into the computer;
combining the 3-D implant plan with information about the desired prosthetic setup and the 3-D representation of the patient anatomy;
designing a temporary healing cap based on the 3-D computer plan of the implant, the desired prosthetic set-up and the 3-D representation of the patient anatomy, the healing cap design including a lower, sub-gingival part, a coronal part and a marginal edge, the marginal edge and the lower sub-gingival part being a function of the desired outcome wherein the marginal edge further comprises a transition between the lower sub-gingival part and the coronal part of the healing cap at the gum level;
the designing step further including defining said coronal part of the temporary healing cap to extend cranially with respect to the marginal edge so as to attain a dome-like shape having no protrusions or substantially no protrusions in order to allow the use of a removable prosthesis during healing, wherein a surface curvature of the gum at said implantation site is used to define the dome-like shape;
storing the marginal edge and the lower sub-gingival part of the healing cap in a memory of the computer; and
wherein the temporary healing cap is configured to support and shape the soft tissue according to the emergence profile determined by the 3-D implant plan for prosthetic restoration.

18. The method of claim 17 wherein the lower sub-gingival part of the healing cap is adapted to apply or reduce pressure on soft tissue, including gums, to shape the soft tissue.

19. The method of claim 17 further comprising a step for manufacture of the healing cap selected from the group consisting of CNC milling, Rapid Prototyping, Rapid Manufacturing, and layered manufacturing.

20. The method of claim 17, wherein in the designing step, the marginal edge is shaped according to an expected shape of the soft tissue after healing.

21. A method for soft tissue management using a custom healing cap for dental implantology, comprising the steps of:
providing a temporary custom healing cap, the custom healing cap designed by scanning an implantation site or an impression of the implantation site; creating a 3-D computer plan of a digital implant comprising digital representations of possible positions of the digital implant in the mouth of the patient based on a first grey value data scan of the patient, the grey value data scan providing gray value data wherein the grey value data includes information about a thickness and/or a profile of the soft tissue of the patient along a jaw line prior to dental implant placement,
loading the 3-D implant plan into a computer,
providing information about a desired prosthetic set-up,
loading the information about a desired prosthetic set-up into the computer,
providing a 3-D representation of the patient anatomy,
loading the 3-D representation of the patient anatomy into the computer,
designing a healing cap based on the 3-D implant plan, the desired prosthetic set-up and the 3-D representation of the patient anatomy, the healing cap design including a desired marginal edge, wherein the desired marginal edge further comprises a transition between a lower, sub-gingival part of the healing cap and a coronal part of the healing cap, the marginal edge defining a closed 3-D curve at the gum level, the designing step further including defining said coronal part of the healing cap to extend cranially with respect to the desired marginal edge so as to attain a dome-like shape having no protrusions or substantially no protrusions in order to allow the use of a removable prosthesis during healing, wherein a surface curvature of the gum at said implantation site is used to define the dome-like shape;

storing the desired marginal edge in a memory of the computer, and processing the designed healing cap and sending it to one of computer driven manufacturing equipment or rapid prototyping/rapid manufacturing machines;

selecting one of the digital representations of possible positions of an implant in the mouth of the patient and implanting the implant in a jawbone of the patient in the position of the selected digital representation; and placing the temporary custom healing cap processed in the processing step over the implant immediately after the step of implanting the implant, the temporary custom healing cap supporting and shaping the soft tissue according to the desired prosthetic set-up which includes a desired emergence profile for the prosthetic.

22. The method of claim 21 further including the additional steps of: removing the temporary custom healing cap from the abutment after shaping the soft tissue to a desired contour in the healing phase of the implant; and installing a prosthetic over the abutment after removal of the temporary healing cap.

23. The method of claim 22 wherein the prosthetic is selected from the group consisting of a prosthetic tooth and a crown.

* * * * *